United States Patent [19]

Quinn et al.

[11] Patent Number: 5,093,371

[45] Date of Patent: Mar. 3, 1992

[54] NAPHTHYL KETONE INHIBITORS OF CHOLESTEROL ESTERASE AND THEIR USE AS HYPOLIPIDEMIC AND HYPOCALORIC AGENTS

[75] Inventors: Daniel M. Quinn; Gialih H. Lin, both of Iowa City, Iowa

[73] Assignee: University of Iowa Research Foundation, Iowa City, Iowa

[21] Appl. No.: 546,910

[22] Filed: Jul. 2, 1990

[51] Int. Cl.$^5$ .............................................. A61K 31/12
[52] U.S. Cl. ..................................... 514/682; 568/328
[58] Field of Search ......................... 568/328; 514/682

[56] References Cited

U.S. PATENT DOCUMENTS 3,641,161  2/1972  Fried et al. ........................... 568/328
4,288,453  9/1981  Vincent et al. ....................... 562/470
4,803,013  2/1989  Yokoyama ............................. 568/327

OTHER PUBLICATIONS

Sohl, Julie, et al., "Haloketone Transition State Analog Inhibitors of Cholesterol Esterase", *Bioch. & Biophy. Res. Comm*, vol. 151, No. 1, Feb. 29, 1988, pp. 554–560.

*Primary Examiner*—James H. Reamer
*Attorney, Agent, or Firm*—Zarley, McKee, Thomte, Voorhees & Sease

[57] ABSTRACT

Certain 2-naphthyl ketones are used as inhibitors of cholesterol esterase and function as hypolipidemic and hypocaloric agents. The invention also relates to a method of decreasing the absorption of dietary cholesterol and fats through the wall of the intestinal tract.

16 Claims, 2 Drawing Sheets

NAPHTHYL KETONE INHIBITORS OF CHOLESTEROL ESTERASE AND THEIR USE AS HYPOLIPIDEMIC AND HYPOCALORIC AGENTS

BACKGROUND OF THE INVENTION

Pancreatic cholesterol esterase (CEase) is a lipolytic enzyme that catalyzes the hydrolysis of cholesteryl esters, phospholipids and triacylglycerols in the intestinal tract. The enzyme may play a role in the absorption of dietary cholesterol across the intestinal mucosa and eventually into the bloodstream, though certain literature teaches away from this physiological role, Watt and Simmons, J. Lipid Res., 22, 157–165 (1981). Given the legendary connection between blood serum cholesterol levels and atherosclerosis, it is reasonable to suspect that reagents that specifically and rapidly inhibit CEase may be worthy of investigation for use in the prophylaxis and/or treatment of the disease. Such agents would be of enormous benefit to the United States and other industrialized societies where atherosclerosis is one of the most prominent causes of death. For example, nearly half of the yearly mortality in the United States results from arteriosclerosis and its sequelae, such as heart attack, stroke, etc. Moreover, the cost to society for surgical and pharmacological management of the disease as well as lost productivity is staggering. It can therefore be seen that there is a continuing, serious and immediate need for development of means of reducing the risk for arteriosclerosis.

One of the often discussed techniques is dietary control. Of course, if diet intake is controlled to reduce the intake of fats, particularly saturated fats, it necessarily follows that the quantity of these materials as absorbed into the blood stream will be decreased. However, such dietary control has proven difficult in modern Western society. Particularly this is true in the United States, where foods are overwhelmingly high in fat content. Thus, for example, in the United States it is generally recognized that high blood cholesterol concentrations provide a significant risk factor in heart disease. It is also generally recognized that the high risk factor for heart disease in the Western world, and particularly the United States is caused by eating foods high in saturated fats, such as many red meats. Accordingly, there is a very real and continuing interest in decreasing either the intake of food substances that have high cholesterol content, or correspondingly in some manner decreasing the absorption rate of the cholesterol and fats through the alimentary tract.

Moreover, since CEase is required for the absorption of dietary fatty acids into the bloodstream, CEase inhibitors may serve as hypocaloric agents (i.e. blockers of the absorption of dietary calories as fat). Such a treatment would be useful in the treatment of obesity, a health problem that afflicts one-third of Americans. It is also a known risk factor in diabetes, atherosclerosis and other life threatening diseases.

It can therefore be seen that there is a real problem, with regard to control of dietary cholesterol. The huge amounts of data documenting the problem suggests the critical need for research and efforts at solving it. There are three possible approaches to lowering blood cholesterol levels for prevention and/or treatment of atherosclerosis: (a) removal of cholesterol from the body; (b) inhibition of de novo cholesterol biosynthesis; (c) prevention of absorption of dietary cholesterol. The first two approaches have been used commercially with some degree of success. For example, the drug Questran ®, which contains the cationic resin cholestyramine, is marketed by Bristol-Myers and lowers blood cholesterol by binding to bile salts in the intestinal lumen. The complex of Questran ® and bile salts is eliminated in the feces, and the liver responds to the loss of bile salts by increasing receptor-mediated uptake of cholesterol ester-rich lipoproteins from the bloodstream. In 1988 Merck, Sharp and Dohme began marketing the HMG-CoA reductase inhibitor Mevacor ®, which prevents cholesterol biosynthesis in the liver. While these efforts are steps along the way, there remains a continuing need for further treatments and approaches.

The third approach, i.e., prevention of absorption of dietary cholesterol, has been largely unexploited as a pharmacological method for treatment of atherosclerosis. One way of prevention of absorption of dietary cholesterol is to cover the walls of the intestinal tract with something which prevents absorption of dietary cholesterol through the intestinal mucosa. This, however, is difficult and not practical because it inhibits the normal digestive process. A far more effective approach would be to develop CEase inhibitors with demonstrated capability of blocking cholesterol absorption. These inhibitors could then be introduced into the alimentary tract through appropriate delivery systems where it would then function to block cholesterol absorption. This invention is predicated upon the discovery of certain novel CEase inhibitors to successfully block cholesterol absorption, to their use for decreasing the absorption of dietary cholesterol and other fats, and to a pharmaceutical composition comprising the active compound in unit dosage formulations.

SUMMARY OF THE INVENTION

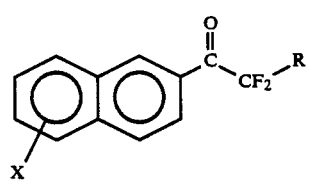

Figure 1:
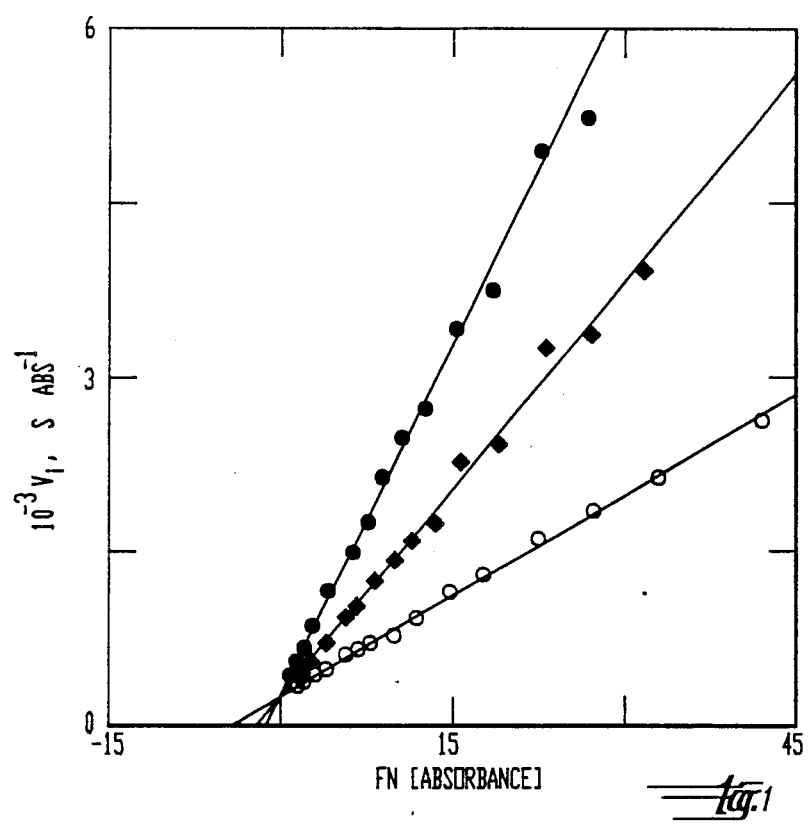
FIG. 1 shows Lineweaver-Burk plots for inhibition of CEase by iododifluoromethyl 2-naphthyl ketone.

wherein X equals hydrogen, lower ($C_1$ to $C_8$) alkyl and oxyalkyl and R is selected from the group consisting of halides, and $C_1$ to $C_8$ alkyl. These are encapsulated in a dose delivery system and administered to decrease the absorption of dietary cholesterol through the intestinal tract. The new compounds have not only been discovered to be cholesterol esterase inhibitors, but this property for these compounds, surprisingly, directly correlates with decreasing the rate of absorption of dietary cholesterol.

DETAILED DESCRIPTION OF THE INVENTION

This invention relates to alpha,alpha difluoro-2-naphthyl ketones that are reversible inhibitors of CEase. Because of the role of CEase in absorption of dietary fats, including cholesterol, these compounds represent a new approach to the design of hypolipidemic and hypocaloric agents. Moreover, in view of the teaching of current literature such as the cited Watt & Simmons article, it is surprising that these compounds function to decrease absorption of dietary cholesterol. Another advantage of the CEase inhibitors of this invention is that they are poorly absorbed into the bloodstream and they are resistant to CEase-catalyzed hydrolysis. Therefore, they pass through the intestinal tract unchanged. And, excess inhibitor should be eliminated in the feces; thus, the problems that attend absorption and systemic distribution should be largely avoided.

To accomplish these advantages, the inhibitors that are described in this invention are designed as structural biomimics of cholesteryl esters. As a result effective dietary cholesterol blockage is achieved with active CEase inhibitors which themselves offer minimum side effect risk when administered.

Compounds useful as CEase inhibitors of this invention are novel $\alpha$, $\alpha$ difluoro-2-naphthyl ketones of the formula:

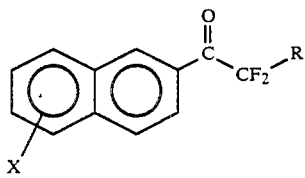

wherein X equals hydrogen, lower ($C_1$ to $C_8$ alkyl and oxyalkyl and R is selected from the group consisting of halides and $C_1$ to $C_8$ alkyl.

Turning back to the general formula for the inhibitors, R is defined as $C_1$ to $C_8$ alkyl, preferably $C_4$ to $C_8$ alkyl. The most preferred compound is 1,1-difluorohexyl 2-naphthyl ketone. These preferred compounds and the most preferred in particular have been found to be most effective CEase inhibitors and correspondingly the most effective dietary cholesterol absorption blockers.

In order to decrease the dietary absorption of cholesterol, fats, phospholipids, etc., the compounds of the present invention must be administered in a small but effective cholesterol esterase inhibiting amount. The usual method of administration is orally into the alimentary tract in a unit dosage form. In such systems, the active compound is combined with a pharmaceutical carrier, with the active compound dosed to provide a level ranging from 0.01 mg to about 1.0 mg per kg of body weight.

Pharmaceutical carriers which are acid resistant to the acid pH of the stomach (normally is about 2) may be used. They also should be nondigestable to the enzyme pepsin which is present in the stomach. There are commercially available solid pharmaceutical carriers which are resistant to stomach degradation and will pass through to the small intestine where the bile in the intestine which is more lipophilic will dissolve them. See for example Viokase and Entozyme that are marketed by A. H. Robins Company of Richmond, Va. These compounds are examples of carriers that dissolve in the small intestine but not in the stomach. Another potential coating is marketed by Lactaid, Inc. of Pleasantville, N.J. The preferred carriers are solid carrier materials, and flavor materials may be added to those.

Solid pharmaceutical carriers such as starch, sugar, talc, mannitol and the like may be used to form powders. Mannitol is the preferred solid carrier. The powders may be used as such for direct administration or, instead, the powder may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form tablets.

Unit dosage forms such as tablets and capsules may contain any suitable predetermined amount of the active naphthyl ketone and may be administered one or more at a time at regular intervals. Such unit dosage forms, however, should generally contain a concentration of 0.1% to 10% by weight of the tablet of one or more of the active compounds.

|   | Mg. |
|---|---|
| 1. Active 2-naphthyl ketone | 12.5 |
| 2. Mannitol | 100 |
| 3. Stearic acid | 3 |

A granulation is made from the mannitol. The other ingredients are added to the dry granulation and then the tablets are punched.

Another tablet may have the compositions:

|   | Mg. |
|---|---|
| 1. Active-2-naphthyl ketone | 10 |
| 2. Starch U.S.P. | 57 |
| 3. Lactose U.S.P. | 73 |
| 4. Talc U.S.P. | 9 |
| 5. Stearic acid | 6 |

Powders 1, 2 and 3 are slugged, then granulated, mixed with 4 and 5, and tableted.

Capsules may be prepared by filling No. 3 hard gelatin capsules with the following ingredients, thoroughly mixed:

|   | Mg. |
|---|---|
| 1. Active-2-naphthyl ketone | 5 |
| 2. Lactose U.S.P. | 200 |
| 3. Starch U.S.P. | 16 |
| 4. Talc U.S.P. | 8 |

As earlier explained, there are certain of the compounds falling within the general formula which are preferred. The preferred compounds have been selected on the basis of structure reactivity studies. Generally, those which are most preferred are those which have a straight alkyl chain of six to eight carbons in length, attached to the fused ring system. The method of preparation of these compounds involves fairly routine synthesis procedures, known to those of skill in organic synthesis. However, the scheme for synthesizing these compounds is set forth below.

SCHEME

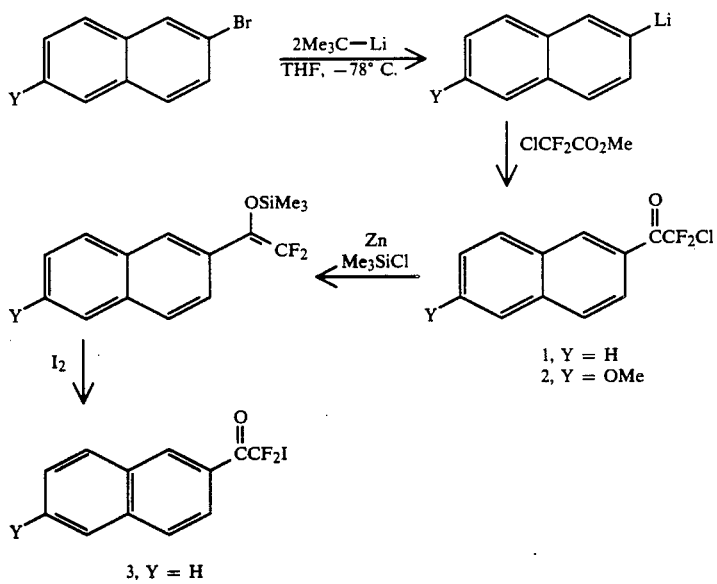

1, Y = H
2, Y = OMe

3, Y = H

Generally speaking, the procedure as above outlined involves four steps. The scheme outlines the structural classes of difluoroketone inhibitors of CEase that are the subjects of this disclosure. They show the typical synthetic procedures used in our laboratories to synthesize α,α-difluoroketones, and highlights the structures of the inhibitors (compounds 1-3). The synthesis of 2-naphthyl halomethyl ketones is outlined in the reaction shown above and involves the following: (1) transmetallation of 2-naphthylbromide with t-butyllithium at low temperature; (2) reaction of the resulting 2-naphthyl lithium with methyl chlorodifluoroacetate to produce inhibitors 1 and 2; (3) if desired, conversion of inhibitors 1 and 2 to the corresponding silyl enolates by treatment with trimethylsilyl chloride in the presence of metallic zinc followed by (4) production of the iododifluoroketone inhibitor 3 by treatment of the trimethylsilyl enolate with iodine.

The synthesis of additional alkyl difluoroketone inhibitors of CEase (compounds 4-6) involves the following steps: (1) transmetallation of 6-substituted 2-naphthylbromides with t-butyllithium at low temperature; (2) conversion of 2-naphthyl lithiums to the target ketones by reaction with α,α-difluoroalkyl ethyl esters. This procedure was used to synthesize inhibitors 4-6.

The CEase-catalyzed hydrolysis of the water-soluble substrate p-nitrophenyl butyrate (PNPB) is a reaction that is routinely used to characterize inhibitors. The reaction is followed at 25.0±0.1.C and pH 7.3 in 0.1 M sodium phosphate buffer that contains 0.1 N NaC1, 1 mM Triton X100, and the appropriate concentrations of CEase and PNPB. Inhibitor characterization occurs in two stages: (a) the form of the inhibition is determined by fitting substrate timecourse data to the integrated form of the Michaelis-Menten equation by nonlinear-least squares methods:

$$t = \frac{K_m}{V_{max}} \ln \frac{[S]_o}{[S]} + \frac{1}{V_{max}} ([S]_o - [S]) \quad (1)$$

Reactions are run in the absence and presence of inhibitor. Lineweaver-Burk plots of the data are constructed, as shown in FIG. 1 for inhibition by iododifluoromethyl 2-naphthyl ketone. (b) The dissociation constant of the CEase-inhibitor complex, $K_i$, is determined by one of two methods. In the first (Method A), $K_m$ is calculated from a replot of the apparent $K_m$ values (determined by fitting timecourses to equation (1)) versus inhibitor concentration. The replot is described by equation 2:

$$K_m^{app} = K_m + K_m \frac{[I]}{K_i} \quad (2)$$

Figure 2:
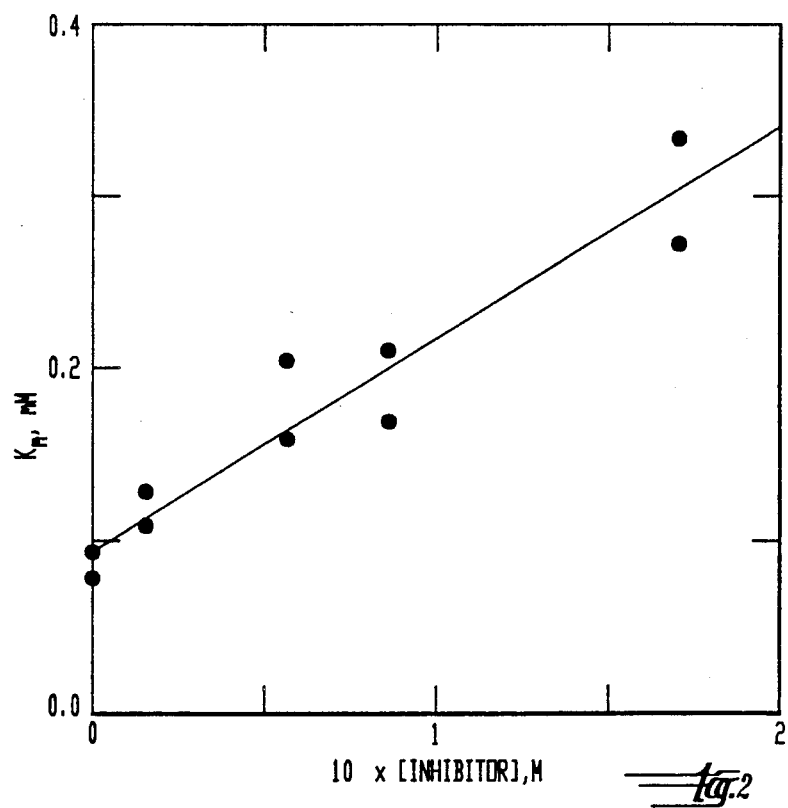
FIG. 2 shows a linear-least squares fit of data from FIG. 1 to equation (2) set forth below.

FIG. 2 shows such a replot according to equation 2 for inhibition by iododifluoromethyl 2-naphthyl ketone. In the second approach (Method B), initial velocity (Vi) versus inhibitor concentration data are fit by nonlinear-least squares to equation 3:

$$V_i = \frac{V_o K_i^{app}}{K_i^{app} + [I]} \quad (3)$$

Figure 3:
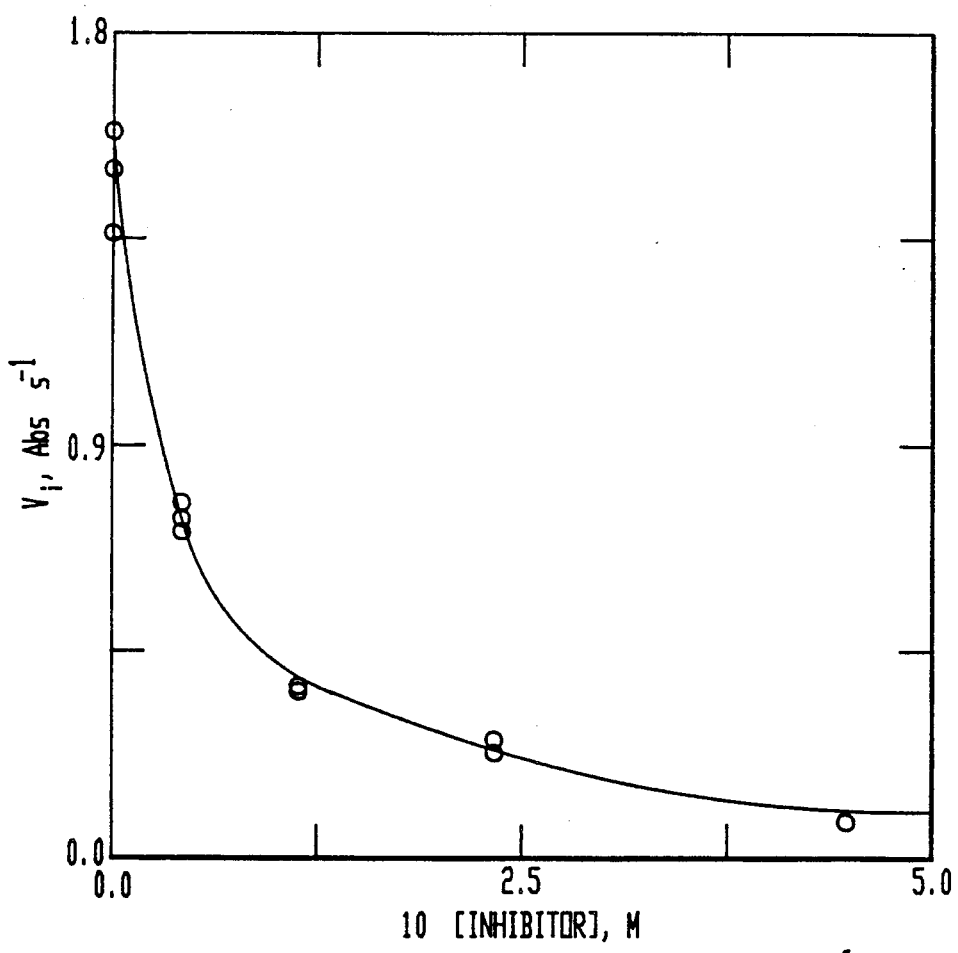
FIG. 3 shows a nonlinear-least squares fit of initial velocities versus inhibitor concentration to equation (3) set forth below for inhibition of CEase by 1,1-difluoropentyl 2-(6-methoxy)naphthyl ketone.

FIG. 3 shows a fit to equation 3 of data for inhibition by 1,1-difluoropentyl B-(6-methoxy)naphthyl ketone. The apparent $K_i$ is then used to calculate the actual $K_i$ from equation 4:

$$K_i = K_i^{app}/(1+[S]/K_m) \quad (4)$$

In equation 4 [S] is the concentration of the substrate PNPB and $K_m$, the Michaelis constant for CEase-catalyzed hydrolysis of PNPB, is 0.09 mM.

The following examples are offered to further illustrate but not limit the scope of the present invention. It should be understood that reasonable modifications, both the processes and the compounds, can be made without departing from the scope and spirit of the invention, and those reasonable modifications are intended to be included within the scope of the present invention.

EXAMPLES

Using the procedures outlined in the scheme illustrated above, the six CEase inhibitors listed in Table I below were prepared, and their structures confirmed. Operation conditions for each varied in only minor aspects.

Table I lists $K_i$ values and demonstrate that $\alpha,\alpha$-difluoro-2-naphthyl ketones are potent reversible inhibitors of CEase. Moreover, the most potent inhibitor (compound 6) has an alkyl chain of 7 carbons in length, and hence closely structurally resembles cholesteryl esters. The $\alpha,\alpha$-difluoro alkyl chain mimics the fatty acyl portion of the cholesteryl ester, while the fused naphthyl ring system mimics the A and B rings of the steroid portion of the cholesteryl ester.

In summary, the studies outlined in this invention disclosure describe the successful development of potent difluoroketone transition state analog inhibitors of CEase.

TABLE I

Inhibition Constants for Difluoroketone Inhibitors of Cholesterol Esterase

| Inhibitor | $K_i$, M |
|---|---|
| Chlorodifluoromethyl 2-Naphthyl Ketone (1) | $2.0 \pm 0.3 \times 10^{-6}$ |
| Chlorodifluoromethyl 2-(6-Methoxy)naphthyl Ketone (2) | $6 \pm 1 \times 10^{-6}$ |
| Iododifluoromethyl 2-Naphthyl Ketone (3) | $8 \pm 1 \times 10^{-7}$ |
| 1,1-Difluoropentyl 2-Naphthyl Ketone (4) | $2.7 \pm 0.5 \times 10^{-7}$ |
| 1,1-Difluoropentyl 2-(6-Methoxy)naphthyl Ketone (5) | $3.8 \pm 0.7 \times 10^{-7}$ |
| 1,1-Difluorohexyl 2-Naphthyl Ketone (6) | $8 \pm 1 \times 10^{-8}$ |

The data presented in Table I show that the inhibitors of the present invention are useful reversible inhibitors of CEase. The data indicate the compounds to be useful as CEase inhibitors in animals, and absorption blockers for dietary cholesterol and fats.

In sum, it therefore can be seen as illustrated by the specification, the drawings, and the examples, that applicant has provided a group of highly useful 2-Naphthyl ketones having utility as effective CEase inhibitors which can be used to effectively decrease the rate and amount of absorption of dietary cholesterol.

What is claimed is:

1. A 2-naphthyl ketone of the formula:

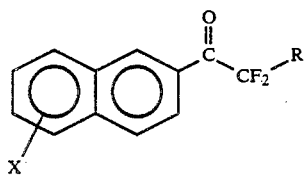

wherein X is selected from the group consisting of hydrogen, $C_1$ to $C_8$ alkyl and $C_1$ to $C_8$ oxyalkyl, and R is $C_4$ to $C_8$ alkyl.

2. A 2-naphthyl ketone of claim 1 wherein X is hydrogen.

3. A compound of claim 1 wherein R is $C_5$ alkyl.

4. A compound of claim 1 wherein X is $C_1$ to $C_8$ oxyalkyl.

5. A method of decreasing the absorption of dietary cholesterol and fats through the wall of the intestinal tract, said method comprising:
   administering to a mammal a small but cholesterol esterase inhibiting effective amount of a compound of the formula:

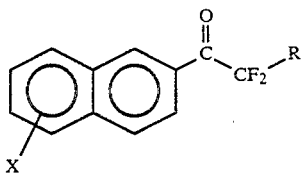

wherein X is selected from the group consisting of hydrogen, $C_1$ to $C_8$ alkyl and $C_1$ to $C_8$ oxyalkyl, and R is selected from the group of halides, and $C_1$ to $C_8$ alkyl.

6. A method of claim 5 wherein R is $C_4$ to $C_8$ alkyl.

7. A method of claim 6 wherein X is hydrogen.

8. A method of claim 7 wherein R is $C_4$ to $C_8$ alkyl.

9. A method of claim 8 wherein R is $C_5$ alkyl.

10. A method of claim 5 wherein X is C to $C_8$ oxyalkyl.

11. A unit dosage pharmaceutical composition comprising a pharmaceutical carrier and from 0.01 mg to 1.0 mg/kg of body weight of a difluoroketone of the formula:

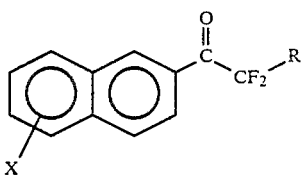

wherein X is selected from the group consisting of hydrogen, $C_1$ to $C_8$ alkyl and $C_1$ to $C_8$ oxyalkyl, and R is selected from the group of halides, and $C_1$ to $C_8$ alkyl.

12. A composition of claim 11 wherein R is $C_4$ to $C_8$ alkyl.

13. A composition of claim 12 wherein X is hydrogen.

14. A composition of claim 13 wherein R is $C_4$ to $C_8$ alkyl.

15. A composition of claim 14 wherein R is $C_5$ alkyl.

16. A composition of claim 11 wherein X is $C_1$ to $C_8$ oxyalkyl.

* * * * *

UNITED STATES PATENT AND TRADEMARK OFFICE
CERTIFICATE OF CORRECTION

PATENT NO.  : 5,093,371
DATED       : March 3, 1992
INVENTOR(S) : Daniel M. Quinn and Gialih H. Lin It is certified that error appears in the above-identified patent and that said Letters Patent is hereby corrected as shown below:

In the patent, column 1, before the "Background of the Invention", please insert the following Grant Reference:

--GRANT REFERENCE
    This invention was made with government support under Contract No. HL-30089 awarded by the National Institutes of Health.  The Government has certain rights in the invention.--

Signed and Sealed this

Seventeenth Day of August, 1993

Attest:

BRUCE LEHMAN

Attesting Officer

Commissioner of Patents and Trademarks